(12) United States Patent
Howard

(10) Patent No.: US 11,918,744 B2
(45) Date of Patent: Mar. 5, 2024

(54) THERAPY DELIVERY DEVICE

(71) Applicant: Viomedex Limited, Eastbourne (GB)

(72) Inventor: Stephen Howard, London (GB)

(73) Assignee: VIOMEDEX LIMITED, Eastbourne (GB)

( * ) Notice: Subject to any disclaimer, the term of this patent is extended or adjusted under 35 U.S.C. 154(b) by 686 days.

(21) Appl. No.: 16/347,425

(22) PCT Filed: Nov. 6, 2017

(86) PCT No.: PCT/EP2017/078368
§ 371 (c)(1),
(2) Date: May 3, 2019

(87) PCT Pub. No.: WO2018/083313
PCT Pub. Date: May 11, 2018

(65) Prior Publication Data
US 2019/0275280 A1 Sep. 12, 2019

(30) Foreign Application Priority Data
Nov. 4, 2016 (GB) ...................... 1618649

(51) Int. Cl.
*A61M 16/08* (2006.01)
*A61M 16/06* (2006.01)
(Continued)

(52) U.S. Cl.
CPC .... *A61M 16/0875* (2013.01); *A61M 16/0666* (2013.01); *A61M 16/0683* (2013.01);
(Continued)

(58) Field of Classification Search
CPC .......... A61M 15/0065; A61M 15/0086; A61M 15/009; A61M 16/00; A61M 16/0051;
(Continued)

(56) References Cited

U.S. PATENT DOCUMENTS 3,923,056 A * 12/1975 Bingmann .......... A61M 16/024
128/204.21
3,946,742 A * 3/1976 Eross .................... A61M 25/02
128/DIG. 26
(Continued)

FOREIGN PATENT DOCUMENTS

AU 4683797 A 7/1998
GB 2465358 A 5/2010
(Continued)

OTHER PUBLICATIONS

UK office action for GB1902502.2 dated May 1, 2019.

*Primary Examiner* — Annette Dixon
(74) *Attorney, Agent, or Firm* — Getz Balich LLC

(57) ABSTRACT

A system 10 for delivering respiratory therapy to a patient includes a patient interface device 20 for delivering pressurized gas to a patient, a connector system 60 for connection to a source of pressurized gas and a conduit system 40 fluidly connecting the connector system 60 to the patient interface device 20. The connector system 60 includes a plurality of closable ports 68, 32 that allow a plurality of different modes of respiratory therapy to be provided. The conduit system 40 may include a first gas line 42, a second gas line 46 and a third gas line 46. The second gas line 46 and third gas line 44 may be contained within the first gas line 42 along at least part of their length.

11 Claims, 13 Drawing Sheets

(51) Int. Cl.
*A61M 16/20* (2006.01)
*A61M 39/08* (2006.01)

(52) U.S. Cl.
CPC .... *A61M 16/0816* (2013.01); *A61M 16/0858* (2014.02); *A61M 16/209* (2014.02); *A61M 39/08* (2013.01); *A61M 2039/082* (2013.01); *A61M 2240/00* (2013.01)

(58) Field of Classification Search
CPC ............ A61M 16/0069; A61M 16/024; A61M 16/026; A61M 16/0488; A61M 16/0493; A61M 16/0497; A61M 16/08; A61M 16/0816; A61M 16/0833; A61M 16/0858; A61M 16/10; A61M 16/1045; A61M 16/125; A61M 16/16; A61M 16/205; A61M 16/22; A61M 2016/0021; A61M 2016/0027; A61M 2016/0039; A61M 2016/0042; A61M 2025/022; A61M 2025/024; A61M 2205/15; A61M 25/02; Y10S 128/26; Y10S 128/911
See application file for complete search history.

(56) References Cited

U.S. PATENT DOCUMENTS

| | | | |
|---|---|---|---|
| 3,985,131 A | | 10/1976 | Buck et al. |
| 4,232,667 A | * | 11/1980 | Chalon ................. A61M 16/22 |
| | | | 128/911 |
| 4,676,239 A | * | 6/1987 | Humphrey ............ A61M 16/08 |
| | | | 128/911 |
| 5,404,873 A | * | 4/1995 | Leagre ................. A61M 16/107 |
| | | | 128/203.29 |
| 5,722,391 A | * | 3/1998 | Rosenkoetter ...... A61M 16/085 |
| | | | 128/911 |
| 5,735,271 A | | 4/1998 | Lorenzen et al. |
| 5,823,184 A | | 10/1998 | Gross |
| 5,975,079 A | * | 11/1999 | Hellings ................ A61M 16/06 |
| | | | 128/206.28 |
| 6,014,972 A | * | 1/2000 | Sladek .................. A61M 16/08 |
| | | | 128/203.15 |
| 6,595,214 B1 | | 7/2003 | Hecker et al. |
| 2002/0053345 A1 | * | 5/2002 | Jafari ................. A61M 16/0069 |
| | | | 128/204.23 |
| 2002/0117177 A1 | | 8/2002 | Kwok |
| 2006/0283456 A1 | | 12/2006 | Geiselhart et al. |
| 2009/0133697 A1 | | 5/2009 | Kwok et al. |
| 2012/0080033 A1 | | 4/2012 | Varga et al. |
| 2012/0123208 A1 | | 5/2012 | Remmerswaal et al. |
| 2012/0247480 A1 | | 10/2012 | Varga |
| 2013/0087146 A1 | | 4/2013 | Callaghan et al. |
| 2014/0373834 A1 | | 12/2014 | Gunaratnam et al. |
| 2015/0151063 A1 | | 6/2015 | Hoftman et al. |
| 2015/0335838 A1 | | 11/2015 | Truschel et al. |
| 2016/0022948 A1 | | 1/2016 | Martin et al. |
| 2016/0114118 A1 | | 4/2016 | Gunaratnam et al. |
| 2016/0256646 A1 | | 9/2016 | Vazales |
| 2018/0085544 A1 | | 3/2018 | Holyoake et al. |

FOREIGN PATENT DOCUMENTS

| | | |
|---|---|---|
| WO | 9829153 A1 | 7/1998 |
| WO | 9848878 A2 | 11/1998 |
| WO | 2010099790 A1 | 9/2010 |
| WO | 2014025591 A1 | 2/2014 |

* cited by examiner

THERAPY DELIVERY DEVICE

This application is entitled to the benefit of, and incorporates by reference essential subject matter disclosed in PCT Application No. PCT/EP2017/078368 filed on Nov. 6, 2017, which claims priority GB Patent Appln. No. 1618649.6 filed Nov. 4, 2016, which are hereby incorporated by reference in their entireties.

BACKGROUND OF THE INVENTION

1. Technical Field

The present disclosure relates to ventilation systems for delivering respiratory therapy to a patient.

2. Background Information

Ventilation systems may be used to assist with breathing in humans and other animals experiencing respiratory difficulties. Breathing assistance or respiratory therapy can take a variety of forms depending on the needs of the patient.

One such form of respiratory therapy is continuous positive airway pressure (CPAP) therapy in which respiratory gas, such as air, having a low positive pressure is provided to the patient on a continuous basis in order reduce the work required from the patient for spontaneous breathing. CPAP may be used to treat preterm infants with respiratory distress syndrome, for example. In the case of infant treatment, CPAP is often delivered via a patient interface device, also known as a generator body, which may include nasal prongs or a nasal mask (nasal CPAP or nCPAP). Nasal prongs typically seal against the nares of the infant in order to provide the continuous pressure to the respiratory tract.

Another form of respiratory therapy is high flow therapy in which humidified respiratory gas is delivered to the patient via patient interface device such as a nasal cannula at a high flow rate (for example 1-25 l/min for infants and children). In high flow therapy, the gas outlets of the patient interface device are held loosely in or adjacent to the nasal passage such that there is no seal against the nares to allow exhalation gas and excess inhalation gas flow to escape therearound. The respiratory gas is often heated to prevent irritation to the respiratory tracts. Nasal high flow therapy may also be used to treat infants with respiratory distress syndrome.

Both CPAP and high flow therapy require spontaneous breathing from the patient. In some cases, patients subject to either of these respiratory therapies may stop breathing and require resuscitation. Resuscitation requires administering artificial inflation breaths to oxygenate the patient until spontaneous breathing is restored.

CPAP therapy, high flow therapy and resuscitation require different respiratory gas flow rates and pressures and are often performed using different ventilation systems or equipment.

When administering any of these therapies to an infant the equipment may be bulky in relation to the small size of the patient and may be difficult to secure relative to the infant.

SUMMARY OF THE INVENTION

In accordance with one aspect of the present invention, there is provided a system for delivering respiratory therapy to a patient. The system comprises a patient interface device for delivering pressurized gas to a patient, a connector system for connection to a source of pressurized gas and a conduit system fluidly connecting the connector system to the patient interface device. The system includes a plurality of closable ports that allow a plurality of different modes of respiratory therapy to be provided. The closable ports may be positioned in the connector system or patient interface device or both.

The closable ports allow different gas flow configurations through the system. In particular, the closable ports allow a respiratory gas supply to be connected to the system via at least three different ports or inlets depending on the mode of therapy required. The closable ports also allow the exhaled air from the patient to be vented via at least two different outlets. Varying the route the respiratory gas takes through the system allows a greater range of pressures and flow ranges to be achieved. For example, air can be provided via a small diameter conduit or alternatively through a larger diameter conduit. A smaller diameter conduit might be desirable for delivering CPAP therapy where a lower flow rate is required. A larger diameter conduit might be desirable for delivering highflow or resuscitation therapy where a higher flow rate is required. The invention therefore allows the practitioner to alternate between different modes without removing the ventilation system and replacing it with an alternative system, reducing the equipment required. By using the same system for various modes of therapy, a medical practitioner may be able to switch between the modes more quickly.

In various embodiments, the modes of respiratory therapy include at least two of CPAP (such as nCPAP), high flow therapy and resuscitation ventilation as described above. For example, in one embodiment the ventilation system may allow both CPAP (such as nCPAP) and resuscitation ventilation. In another embodiment, the ventilation system may allow both high flow therapy and resuscitation therapy. In another embodiment, the ventilation system may allow CPAP (such as nCPAP) and high flow therapy. In a preferred embodiment, the ventilation system may allow all three modes; CPAP (such as nCPAP), high flow therapy and resuscitation ventilation. The ability to administer two or more of these modes of therapy may be particularly useful in the treatment of preterm infants with respiratory distress syndrome, for example.

The connector system may be configured such that in, a first mode, one of said plurality of closeable ports is connected to the source of pressurized gas, and in a second mode the same one of said plurality of closeable ports provides an exhaust channel to remove exhaled gases from the system. In other words, a single port of the connector system can be used to provide respiratory gas to the patient or can be used to vent exhaled air. These two functionalities are provided by the ability for the port to be connected to a source of pressurized gas in the first mode and an exhaust port in the second mode. The connector system has at least one alternative port for connection to the source of pressurized gas in the second mode to allow the other port to be used as an exhaust port. In various configurations, the port therefore acts as an air supply port or an exhaust port but not both. In the first mode as described above, the alternative port may be closed by one of the closable ports. In the embodiments described above, a yet further port may be connected to a pressure monitor in the first mode and in the second mode.

In particular embodiments, the connector system may comprise four ports, two of which are closable. For example the connector system may include a first body having a cavity therein. The first body may comprise a first port fluidly connected to the cavity for connection to the conduit system, a second port fluidly connected to the first port via the cavity for connection to a first gas line, such as an exhaust outlet or air supply and a third port for receiving a second gas line from the conduit system such that the second gas line extends from the first port to the third port within the cavity and is not in fluid communication with the cavity. In this embodiment, the third port may include a seal for preventing egress of gas from the cavity via the third port when the second gas line is positioned therein. The connector system may further comprise a fourth port including a first removable closure, the fourth port fluidly connecting the cavity to the external environment when open. The connector system may further include a second body for connection to the second gas line, the second body including a second removable closure for closing the second gas line.

The removable closures may be capable of sealing the ports in one mode but may be adjusted such that the port is opened in another mode. The removable closure may be, for example, a plug or cap which is inserted into the port to seal it and removed from the port to open it. Other temporary closures may include valves, stoppers or seals.

The patient interface device may include two alternative exhaust ports. For example, one of the exhaust ports of the patient interface device may include a temporary closure of the type described above in order to provide alternative flow paths though the ventilation system.

The conduit system may include a first gas line and a second gas line. In particular embodiments the conduit system may further include a third gas line. The second gas line and third gas line (if present) may be contained within the first gas line along at least part of their length.

The second gas line and third gas line may both have an outer diameter that is smaller than an inner diameter of the first gas line. For example, the combined outer diameters of the second gas line and the third gas line may be smaller than the inner diameter of the first gas line in order that both the second gas line and third gas line can fit within the first gas line. Moreover, the fluid conduit provided by the first gas line may have a larger effective cross-sectional area that the conduit defined by the second and/or third gas lines.

In embodiments, the second and third gas lines may each have outer diameters from 3 mm to 15 mm for example from 5 mm to 10 mm. The first gas line may have an inner diameter from 10 mm to 30 mm, for example 15 mm to 20 mm. The first gas line should have sufficient free volume around the second and third gas lines, when contained within, to allow effective exhausting of exhaled and deflected air or supply of respiratory gas. In a preferred embodiment, the second gas line and the third gas line are positioned within the first gas line along the whole length of the first gas line between the patient interface device and connector system. Such an arrangement reduces the number of lines or tubes that need to be handled and fixed relative to the patient resulting in a more compact and easily mounted conduit system. Such an arrangement may be particularly beneficial for smaller patients such as infants.

In an embodiment of any of the above, the patient interface device may comprise a therapy outlet for delivering pressurized air to a patient, a first port for attachment to a first gas line, wherein the first port is in fluid communication with the therapy outlet and a second port for attachment to a second gas line, wherein the second port is in fluid communication with the therapy outlet. Each of the first and second ports may be configured to receive pressurized gas for delivery to the therapy outlet and exhaled gas from the therapy outlet. The second port may be positioned within the first port. Such an arrangement allows the second gas line to be contained within the first gas line at the point of connection between the conduit system and patient interface device, resulting in a more compact arrangement.

The second port may be in fluid communication with the therapy outlet via a channel having a diameter sized such that gas entering the channel from the second port line forms a jet having a greater fluid pressure than gas contained within the second gas line. The channel may have a diameter in the range of 0.1 mm to 3 mm. For example, from 0.3 mm to 1 mm.

In particular embodiments, the patient interface device may further comprise a third port for connection to a pressure monitor and in fluid communication with a pressure outlet adjacent the therapy outlet, wherein the third port is also positioned within the first port. Alternatively or additionally the patient interface device may comprise an auxiliary exhaust port having a removable closure, the auxiliary exhaust port providing an alternative outlet for exhaled air.

The patient interface device may comprise one of a nasal prong device for engaging the nares of a patient, a nasal mask and/or resuscitation mask attached to the therapy outlet. In an embodiment the patient interface device is configured to be interchangeably connected with all three of the above to allow optimization of the various modes of respiratory therapy. For example, the practitioner may wish to use a nasal cannula to administer high flow therapy and switch to nasal prongs or a resuscitation mask during resuscitation.

The system may further comprise a fixation device for securing the patient interface device to the head of a patient.

The system may be configured to deliver respiratory therapy to an infant. For example, the patient interface device may be sized to deliver respiratory therapy to an infant having nares smaller than 5 mm in diameter or smaller than 2 mm in diameter. The ventilation system may be configured to fit an infant having a head size in the range of 15 cm-50 cm in circumference, for example 17 cm-42 cm in circumference.

In accordance with another aspect of the present invention, there is provided a patient interface device for a ventilator system. The patient interface device comprises a therapy outlet for delivering pressurized air to a patient, a first port for attachment to a first gas line, wherein the first port is in fluid communication with the therapy outlet and a second port for attachment to a second gas line, wherein the second port is in fluid communication with the therapy outlet. Each of the first and second ports is configured to receive pressurized gas for delivery to the therapy outlet. The second port is positioned within the first port. For example the first port comprises a substantially circular opening and has a greater diameter than the second port such that the second port is positioned radially within the first port. Positioning of the second port within the first port allows a gas line that is attached to the second port to extend away from the patient interface device within a gas line attached to the first port to thereby provide a more compact system that is easier to handle.

The second port may be in fluid communication with the therapy outlet via a channel having a diameter sized such that gas entering the channel from the second port line forms a jet having a greater fluid pressure than gas contained within the second gas line. The channel may have a diameter in the range of 0.1 mm to 3 mm. For example, from 0.3 mm to 1 mm.

The patient interface device may further comprise a third port for connection to a pressure monitor and in fluid communication with a pressure outlet adjacent the therapy outlet. The third port may also be positioned within the first port to provide a compact system that is easier to handle.

The patient interface device may further comprise an auxiliary exhaust port having a removable closure. The auxiliary exhaust port may provide an alternative outlet for exhaled air when the closure is removed. A further such port may allow further flow configurations within the patient interface device for varying modes of respiratory therapy.

The patient interface may comprise a nasal prong device attached to the therapy outlet for engaging the nares of the patient to deliver nCPAP therapy. In various embodiments, the patient interface device may be sized to deliver respiratory therapy to an infant having nares smaller than 5 mm in diameter or smaller than 2 mm in diameter.

In accordance with another aspect of the present invention, there is provided a connector system for a ventilator system comprising a first body having a cavity therein. The first body comprises a first port, a second port, a third port and a fourth port. The first port is fluidly connected to the cavity for connection to a conduit system. The second port is fluidly connected to the first port via the cavity for connection to a first gas line, such as an exhaust outlet or air supply. The third port is for receiving a second gas line from the conduit system, such that the second gas line extends from the first port to the third port within the cavity. The second gas line is not in fluid communication with the cavity. The third port includes a seal for preventing egress of air from the cavity via the third port when the second gas line is positioned therein. The fourth port includes a first removable closure and fluidly connects the cavity to the external environment when open, such as when the closure is removed. The connector system also comprises a second body for connection to the second gas line. The connector system may be configured such that the second gas line can extend from the third port to the second body for connection thereto. The second body includes a second removable closure for closing the second gas line.

Such a configuration allows the connection of ventilator line in various configurations to vary the flow therethrough. Selective closure of the first and second temporary closures allows further variations of flow through the connector system. By allowing at least two of the ports to act as inlets for respiratory gas and at least two of the ports to act as outlets for exhaust gas such as exhaled air from the patient.

The removable closures may be capable of sealing the ports in one mode but may be adjusted such that the port is opened in another mode. The removable closure may be, for example, a plug or cap which is inserted into the port to seal it and removed from the port to open it. Other temporary closures may include valves, stoppers or seals.

In embodiments, the third port is also configured to receive a third gas line. In such embodiments, the seal prevents egress of gas from the cavity via the third port when the second and third gas lines are positioned therein.

The seal may comprise an insert positioned within the third port or may comprise a plate that is integrally formed with the third port for example.

In accordance with another aspect of the present invention, there is provided a fixation device for securing a ventilation system to the head of a patient. The fixation device comprises a first part for attachment to a respiratory tube of the ventilation system and a second part comprising a first plurality of straps configured to form adjustable loops for attachment to the first part and a second plurality of straps configured to form adjustable loops for attachment to a patient interface device of the ventilation system. The fixation device may be adjusted without removal or movement of the respiratory tube by adjusting the size of at least one of the adjustable loops. A medical practitioner may, therefore improve the fit of the fixation device without moving the ventilation system or interfering with the ventilation system function.

The first plurality of straps may comprise three straps configured to form three adjustable loops for attachment to the first part. Two of the first straps may be configured to extend round the side of the patient's head adjacent each ear for attachment to the second part. Another of the first straps may be configured to extend from adjacent the nape of the neck and over the top of the crown of the patient's head. The second plurality of straps comprises two straps configured to form two adjustable loops for attachment to a patient interface device. The loops formed by the straps may therefore be arranged symmetrically around the respiratory tube to which the fixation device may be attached. This allows the fit of the fixation device to be adjusted without movement of the respiratory tube. In embodiments, the second plurality of straps may be separately formed from the first plurality of straps. These embodiments, the second plurality of straps may be configured to attach to the first straps in order to secure the patient interface device. This may allow the second straps to be provided with the patient interface device and attached thereto for subsequent attachment to the remaining parts of the fixation device. Attachment of the second straps may be by any of the attachment means described below.

The first part may comprise slots for receiving the straps of the second part forming adjustable loops therethrough. For example, the first part may include three slots, each slot receiving a respective strap of the second part. In such an embodiment, two of the three slots may be arranged parallel to one another on the first part, the third slot may be arranged perpendicular to the two parallel slots. For example, the two parallel slots may be configured to receive straps that extend around the side of the patients head over or adjacent to the patients ears. The third slot may be configured to receive a strap that extends up the back of the patient's head from the nape of the neck to the crown.

In embodiments, each of the first and second plurality of straps includes a free distal end, a proximal end and attachment means at its distal end, for attachment to an intermediate part of the respective strap between the distal and proximal ends, in order to form the adjustable loops. In a particular embodiment, the straps are formed from a soft or looped material and the attachment means include a hook material for engagement with the soft or looped material (e.g. a hook and loop fastening tape). Alternative attachment means may include adhesives, clips or buttons.

The second part may comprise fixation means for attachment of the fixation device to the ventilation system. The fixation means may include a hook and loop material. In one embodiment, the fixation means may additionally, or alternatively, comprise a removable fixation member comprising a substantially U-shaped block forming an opening for receiving a tube of the ventilation system.

In accordance with a further aspect of the present invention there is provided a system for delivering a plurality of modes of respiratory therapy to a patient comprising a patient interface device and connector system as described in any of the aspects or embodiments above. The ventilation system further comprises a conduit system fluidly connecting the connector system to the patient interface device. The ventilation system may further comprise a fixation device as described in any of the aspects or embodiments above.

In accordance with a further aspect of the present invention there is provided a system for delivering a plurality of modes of respiratory therapy to a patient comprising a patient interface device and fixation device as described in any of the aspects or embodiments above. The patient interface device comprises first and second apertures for engaging the two adjustable loops formed by the second plurality of straps. The system may further comprise a connector system, as described in any of the aspects or embodiments above.

In accordance with a further aspect of the present invention there is provided a system for delivering a plurality of modes of respiratory therapy to a patient comprising a patient interface device, as described in any of the aspects or embodiments above.

In accordance with a further aspect of the present invention there is provided a system for delivering a plurality of modes of respiratory therapy to a patient comprising a connector system, as described in any of the aspects or embodiments above.

In accordance with a further aspect of the present invention there is provided a system for delivering a plurality of modes of respiratory therapy to a patient comprising a fixation device, as described in any of the aspects or embodiments above.

In accordance with a further aspect of the present invention there is provided a method of providing a plurality of modes of respiratory therapy including providing a first mode of respiratory therapy using a ventilation system and adjusting the direction of flow, opening a port, or connecting the gas supply through an alternative port of the ventilation system to provide a second mode of respiratory therapy.

The first mode and second modes may include CPAP (such as nCPAP), high flow therapy and resuscitation ventilation as described above.

In embodiments, adjusting the direction of flow through the ventilation system may include opening a valve of a connector system. Adjusting the direction of flow may also or alternatively include removing a respiratory gas supply line from one port and connecting it to another port of the ventilation system.

The method may include providing a system as described in relation to any of the embodiments above, connecting a respiratory gas supply to one port of the connector system to provide one of CPAP, high flow or respiratory therapy then switching to another one of CPAP, high flow or respiratory therapy by connecting the gas supply to another port of the connector system and/or by opening another port to exhaust gases from the system.

Additionally or alternatively, switching between the modes of therapy may include switching on a further gas supply, optionally having a higher pressure and/or flow rate than the first gas supply, which is connected to the system during the first mode of therapy. The further gas supply may have been isolated from the system by a switch, valve or flow prevention means during the first mode. Once the further gas supply is switched on, the initial gas supply may be switched off or may remain on (i.e. in fluid communication with the system). These embodiments allow switching between modes simply by actuating a switch or valve of the further gas supply and requires no reconnection of the conduit system or gas supplies between modes.

A closable port of the system may be operated during a resuscitation mode. For example the closable port may be closed to inflate the patient's lungs and may be opened to deflate the lungs.

BRIEF DESCRIPTION OF THE DRAWINGS

Some embodiments of the disclosure will now be described by way of example only and with reference to the accompanying drawings in which.

DETAILED DESCRIPTION

Figures 1A, 1B:
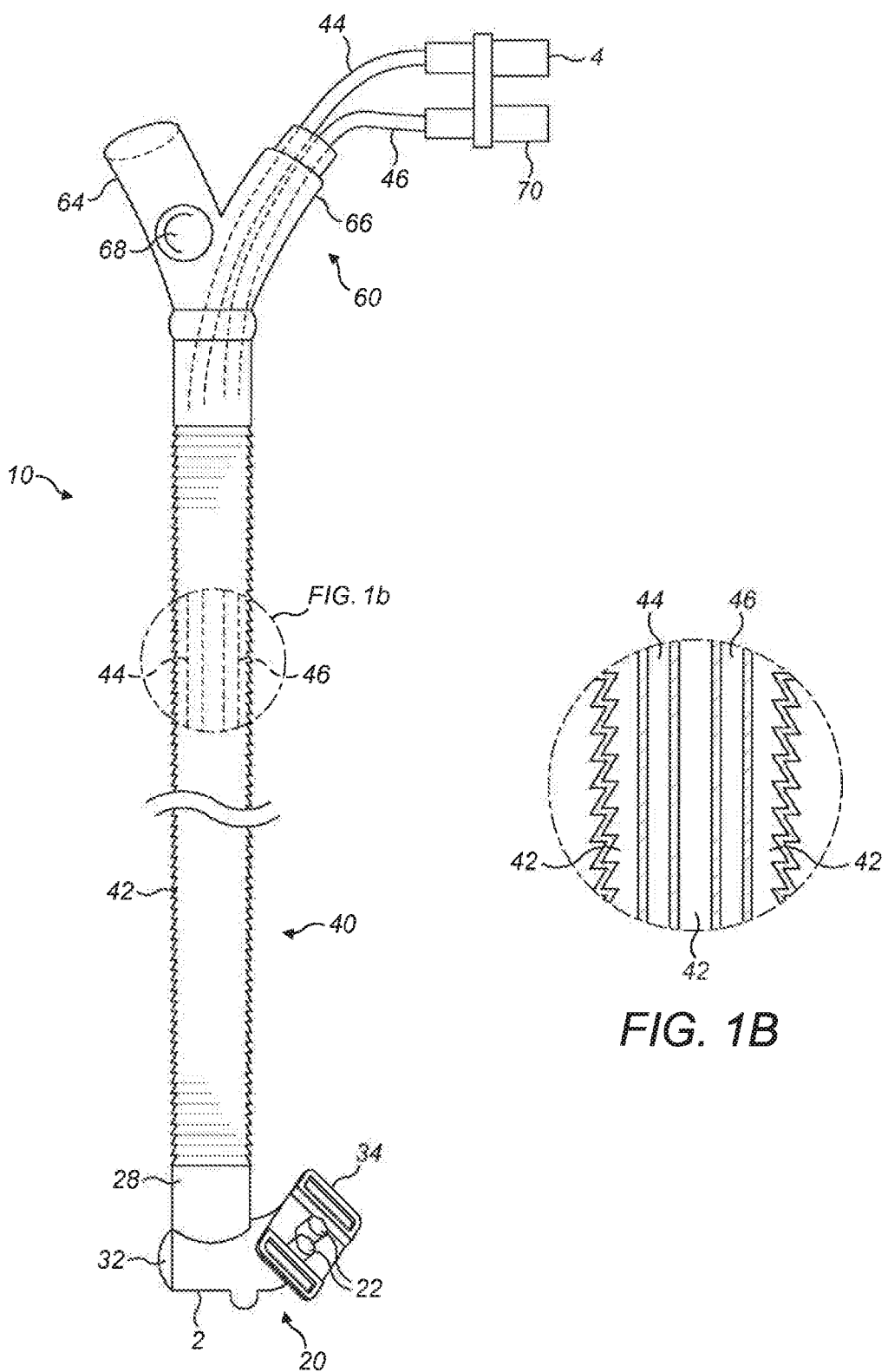
FIG. 1A shows a ventilator system according to an embodiment of the invention.
FIG. 1B shows a cross-sectional detail view of the conduit system of FIG. 1A.

With reference to FIG. 1, an exemplary ventilation system 10 is illustrated. The ventilation system is configured to provide respiratory therapy to an infant such as a pre-term, neonatal infant. In particular the ventilation system 10 is configured to provide CPAP therapy to infants. The ventilation system is also adaptable to provide high flow therapy and resuscitation to infants.

The ventilation system 10 has a patient-facing or distal end 2 and a caregiver-facing or proximal end 4. The ventilation system includes a patient interface device 20 at its distal end 2 and a connector system 60 at its proximal end 4. The patient interface device 20 and connector system 60 are fluidly connected to each other via a conduit system 40 therebetween. That is, the conduit system 40 is connected to the patient interface device 20 at its distal end and connected to the connector system 60 at its opposed, proximal end.

The patient interface device 20 is configured to engage with the nares of an infant in order to deliver respiratory therapy thereto. The conduit system 40 includes an first gas line 42 for exhausting exhaled air from the patient (in CPAP mode), second gas line 46 for providing pressurized air to the patient interface device (in CPAP mode) and a third gas line 44 for monitoring air pressure within the patient interface device 20 and thereby allowing the control and/regulation of the respiratory therapy. The first gas line 42 may be a resilient, corrugated plastic tube. The connector system 60 is adaptable to allow variation in the modes of respiratory therapy deliverable by the ventilation system 10 as described in more detail below.

Figure 2:
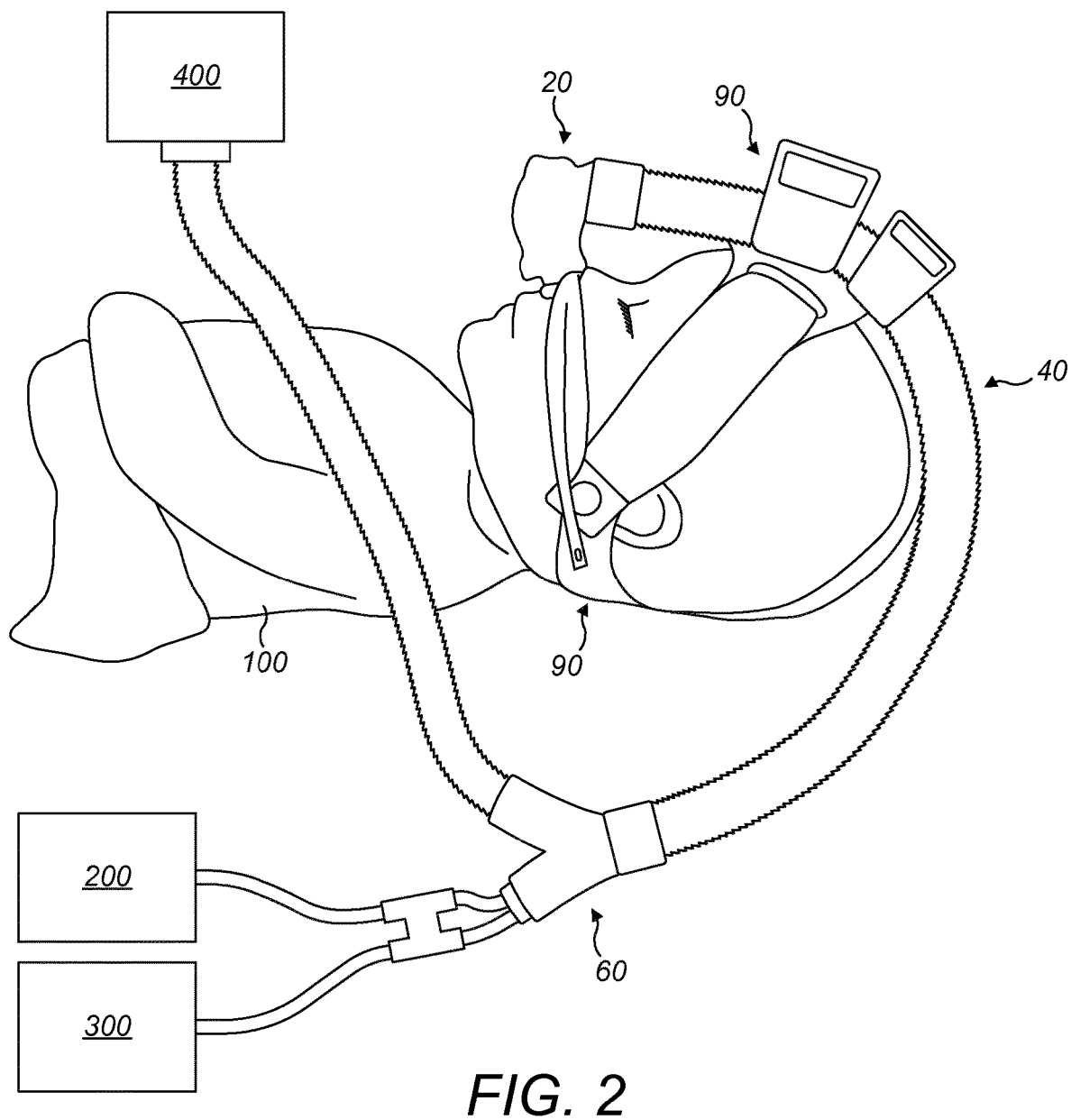
FIG. 2 shows, schematically, the ventilator system of FIG. 1A attached to the head of an infant for providing respiratory therapy.

As shown in more detail in FIG. 1B, the second gas line 46 and third gas line 44 are positioned within the first gas line 42 for a portion of their length. More particularly, they are positioned within the first gas line 42 for their entire length between the patient interface device 20 and connector system 60. The first gas line 42 terminates at the connector system 60. The second gas line 46 and the third gas line 44 extend through the connector system 60 for connection to an air source 200 and pressure monitoring equipment 300, as shown in FIG. 2. However, it will be appreciated that the second and third gas lines 46, 44 could also terminate at the connector system 60 and connect to further conduits provided therein.

The first gas line 42 is attached to the patient interface device 20 via an exhaust port 28. The second gas line 46 and third gas line 44 are attached to the patient interface device 20 via ports positioned within the exhaust port 28, as will be explained in more detail below with reference to FIGS. 3, 4A and 4B. The first gas line 42 is attached to the connector system 60 via a first port 62 through which the air second gas line 46 and third gas line 44 extend, as will be explained in more detail below with reference to FIG. 5.

FIG. 2 shows the ventilation system attached to the head of an infant 100 for delivery of respiratory therapy such as nCPAP thereto. The ventilation system 10 is secured to the head of the infant 100 via a fixation device 90 which circumscribes the head of the infant 100 as will be described below.

Figure 3:
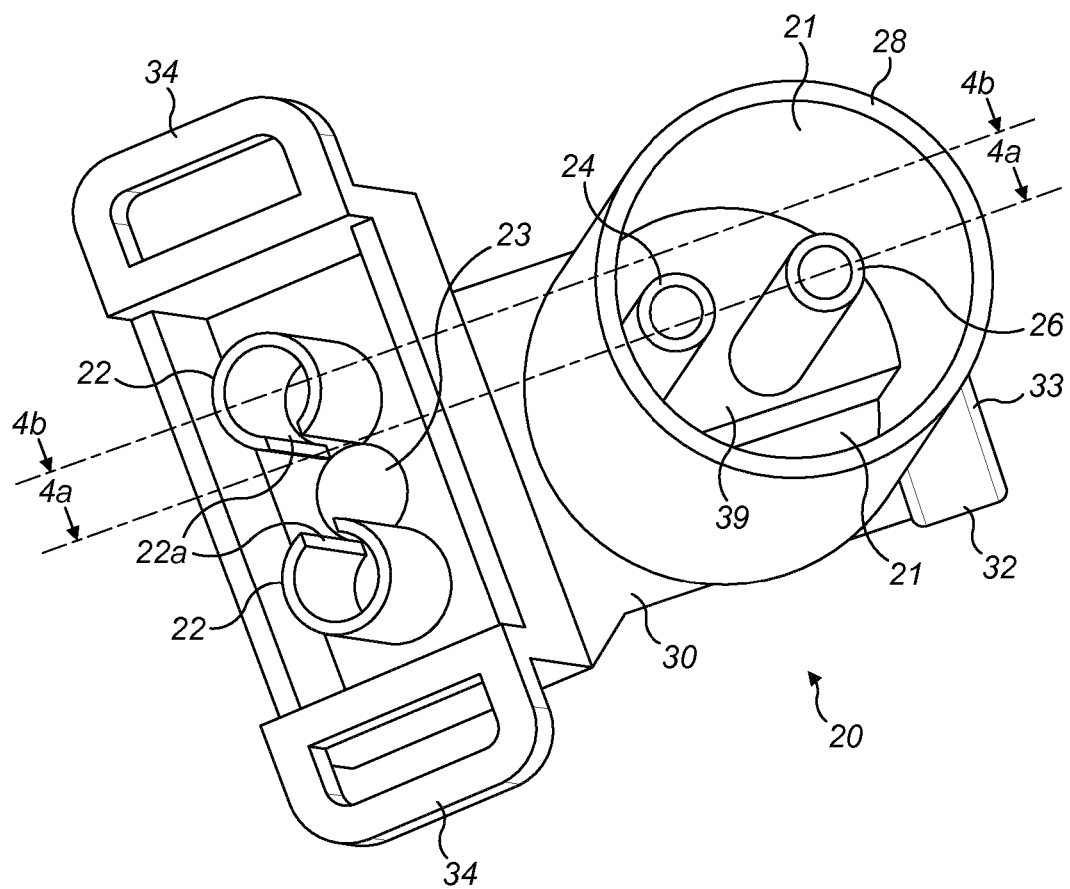
FIG. 3 shows a detail view of a patient interface device according to an embodiment of the invention.
Figure 4A:
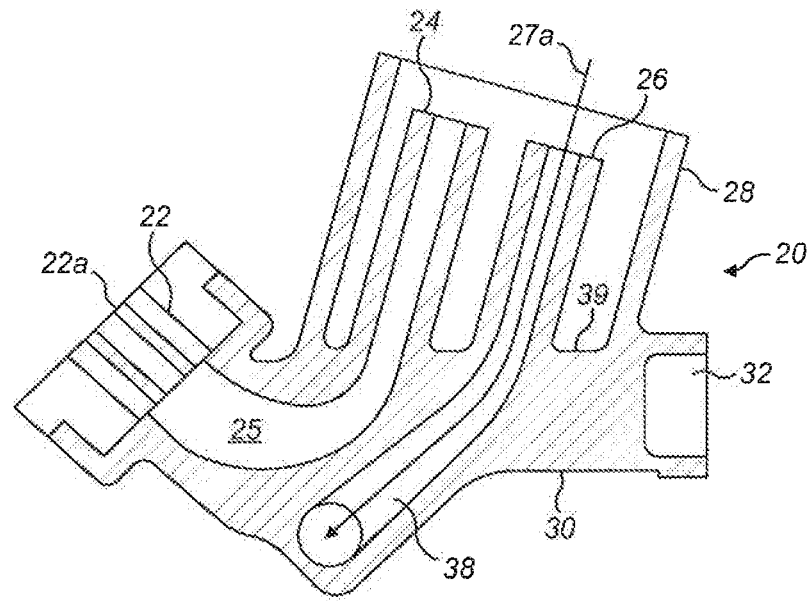
FIG. 4A show a cross-sectional view through the center of the patient interface device of FIG. 3.
Figure 4B:
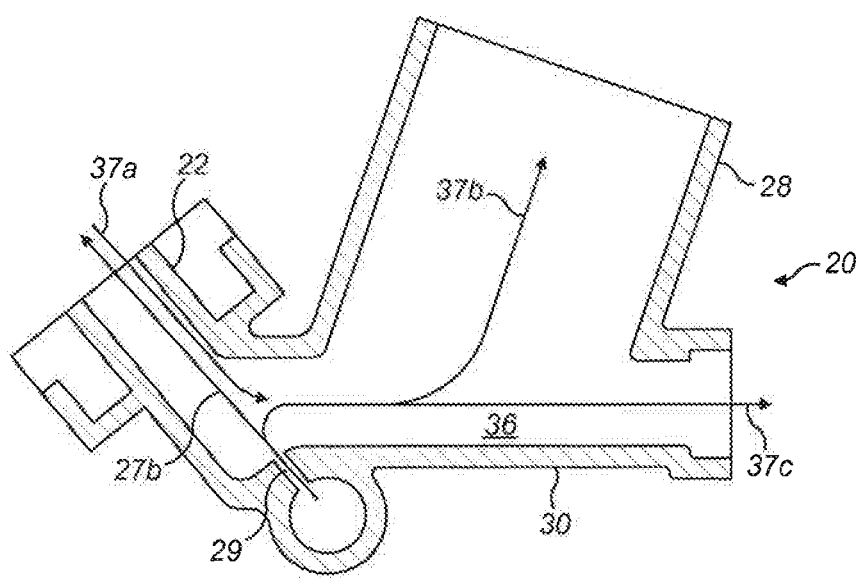
FIG. 4B shows an off-center cross-sectional view of the patient interface device taken to one side of the pressure and inlet ports.

FIGS. 3, 4A and 4B show the patient interface device 20 of the ventilator system 10 described above. The patient interface device 20 is in the form of a nasal prong device for delivering pressurized air to the nares of an infant 100. The patient interface device includes a main body 30 having an internal cavity 36 and first and second fluid passages 25, 27 (shown in detail in FIG. 4A). A pressure port 24 is suitable for connection with a third gas line 44, as described above. An air supply port 26 is suitable for connection with a second gas line 46 as described above and is fluidly connected to the cavity 36 via a second fluid passage 27. An exhaust port 28 is suitable for connection with the first gas line 42. The pressure port 24 and air supply port 26 are positioned within and surrounded by the exhaust port 28, i.e. the ports 24, 26 are located radially within the exhaust port 28, reactive to the axis along which the exhaust port 28 extends. More specifically, the pressure port 24 and air supply port 26 comprise conduits supported within the exhaust port 28 by a strut 39. The strut 39 extends from one side of the exhaust port 28 to the opposite side thereof. Two gaps 21 are positioned either side of the strut 39 within the exhaust port 28 to allow gas to flow out of the exhaust port 28, around the strut 39, pressure port 24 and air supply port 26.

The patient interface device further includes two air outlets (or therapy outlets) 22 which are configured for connection to nasal prongs (not shown) to provide airflow to the nares of an infant 100. The nasal prongs facilitate an airtight seal between the patient interface device 20 and the nares of the patient to provide effective respiratory therapy. An airtight seal is particularly important when administering CPAP therapy.

Respiratory gas is provided at air supply port 26 from the second gas line 46 and is directed along a flow path shown by the arrow 27a to a chamber 38. Gas exits the chamber 38 via two holes 29 that provide a straight conduit for gas in a direction towards each air outlet 22. Each hole 29 is sized sufficiently small such that the gas exiting therefrom forms a fine jet which can reach the nares of the patient 100 via the air outlets 22 along flow path 27b. Each hole has an axis substantially aligned with the axis of the air outlet 22.

When the patient exhales, the jet of air from holes 29 is redirected (or flipped) towards one of the exhaust outlets 28 or 32 along the flow paths shown by the arrows 37, 37b, 37c. The first pressure port 24 is fluidly connected to port 23 (shown in FIG. 3) adjacent the air outlets 22 for measuring the gas pressure at the patient. The port 23 is in fluid communication with, and thus at the same pressure as, the interior of the air outlets 22 via cut outs 22a.

The patient interface device 20 further includes an auxiliary exhaust port 32 with a removable first closure 33. The auxiliary exhaust port 32 is separate from the exhaust port 28 and provides an alternative flow path for exhaled air during respiratory therapy as will be described below. When the first closure 33 is removed, the auxiliary exhaust port 32 establishes a direct flow path between the internal cavity 36 of the patient interface device 20 and the external atmosphere.

Figure 5:
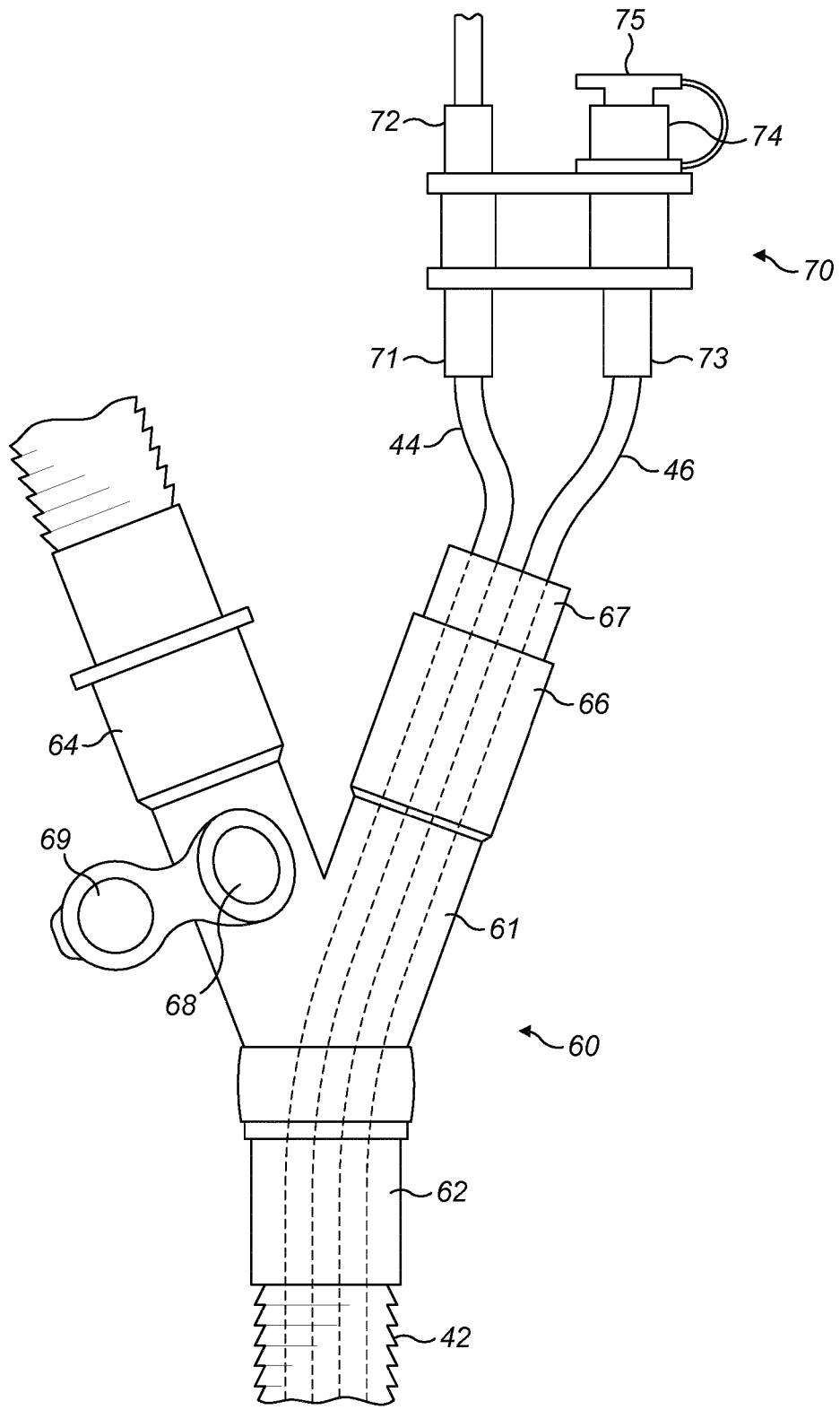
FIG. 5 shows a connector system according to an embodiment of the invention.

FIG. 5 shows a detail view of the connector system 60 of the ventilation system 10 in a resuscitation configuration. The connector system 60 includes a first body 61 that is a hollow connector body having a cavity therein. The first body 61 includes a first port 62 at a first end of the body 61 for connection to the first gas line 42 having the second gas line 46 and the third gas line 44 extending therethrough.

The first body 61 further includes a second port 64 for connection to an exhaust or resuscitation air supply.

A third port 66 contains the second gas line 46 and third gas line 44. A sealing element 67 creates a seal between the cavity of the first body 61 and the third port 66 to prevent gas, such as air, leaking from the cavity to the external environment via the third port 66. It will be appreciated that the third port 66 could be replaced with two ports each containing one of the second gas line 46 and third gas line 44 and each having a seal as described above.

The first body 61 further includes a fourth port 68 with a removable second closure 69. When the second closure 69 is removed from the fourth port 68, the cavity of the first body 61 is in direct fluid communication with the external atmosphere.

The first body 61 may further include a pressure relief valve 600 (shown schematically in FIGS. 10A-C, 11-C and 12).

A second body 70 is a connector body which includes two separate fluid conduits therethrough the first fluid conduit has a distal inlet 71 for connection to the third gas line 44 and a first outlet 72 for connection to a pressure monitoring system (not shown). The second conduit has an inlet 73 for connection with the second gas line 46 and a second outlet 74 for connection with e.g. a CPAP air supply. The second outlet 74 of the second conduit includes a removable third closure 75 for sealing the second outlet 74. The removable third closure 75 is in the form of a plug attached to the second connector body. It is envisaged that other closure means such as flaps or valves might also be used.

Figure 6A:
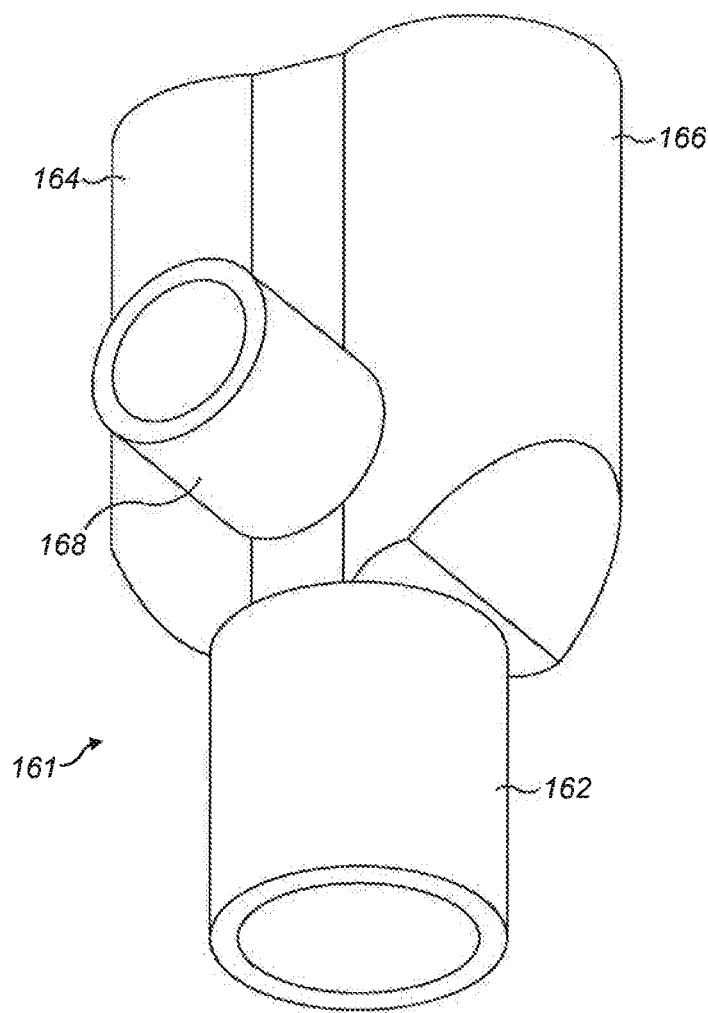
FIG. 6A shows an alternative connector system according to a further embodiment of the invention.
Figure 6B:
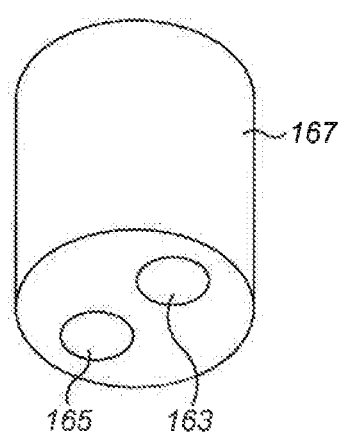
FIG. 6B shows an insert for the connector system of FIG. 6A.

FIG. 6A shows an alternative embodiment of a first body 161 for the connector system 60. The first body 161 of FIG. 6 is substantially the same as the first body 61 of FIG. 5 except that the axes of second and third ports 164 and 166 are substantially parallel. FIG. 6B shows an insert 167 which may be positioned within the port 166 of FIG. 6A to hold and seal the pressure and second gas lines as described above. Such a configuration may be easier to manufacture.

Figure 7A:
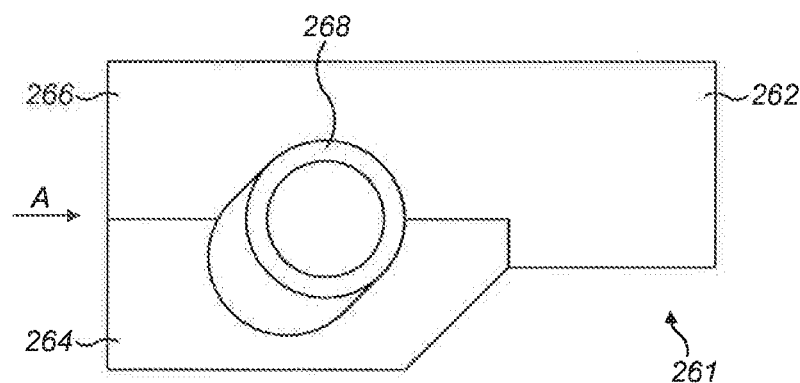
FIG. 7A shows another alternative connector system according to a yet further embodiment of the invention.
Figure 7B:
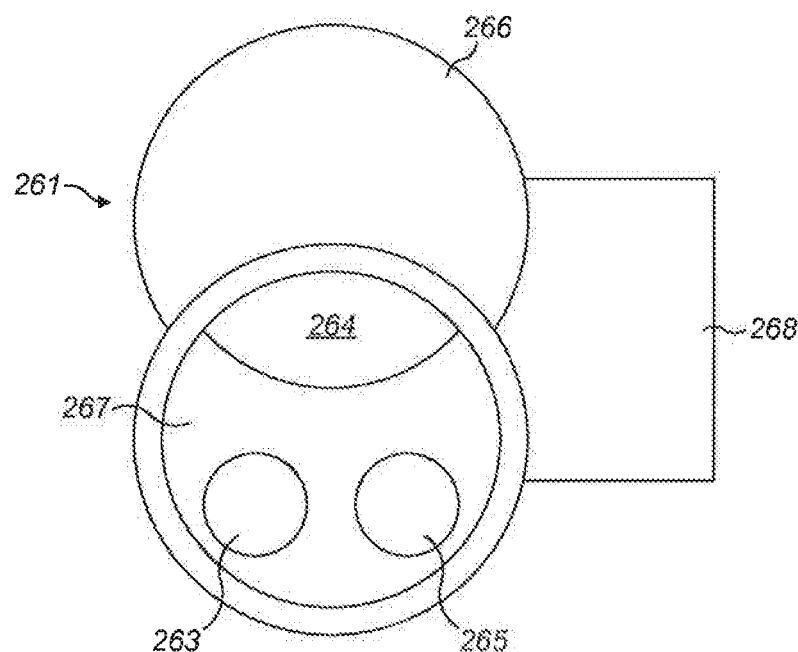
FIG. 7B shows a bottom view of the connector system of FIG. 7A viewed in the direction of arrow A.

FIGS. 7A and 7B show a further alternative embodiment of a first body 261 for the connector system 60. As shown in FIG. 7A, the axes of the first port 262 and third port 266 are aligned to provide a substantially straight path for the second gas line and third gas line from the first port 262 to the third port 266. The second port 264 is parallel to and offset from the first and thirds ports 262, 266. FIG. 7B shows a bottom view of the first body 261 looking into the first port 262. In this embodiment, instead of an insert for positioning and sealing against the third gas line and second gas line, a sealing plate 267 is positioned in the third port 266 and is integrally formed with the first body 261. The sealing plate 267 includes first and second holes 263, 265 each for positioning and sealing against one of a second gas line 46 and a third gas line 44.

FIGS. 8 and 9A to 9E show a fixation device 90 for securing the ventilation system 10 to the head of a patient. The example fixation device 90 is suitable for attachment to the head of an infant 100 however it will be appreciated that such a fixation device 90 could be easily adapted for use with an adult by adjusting the dimensions accordingly.

Figure 8:
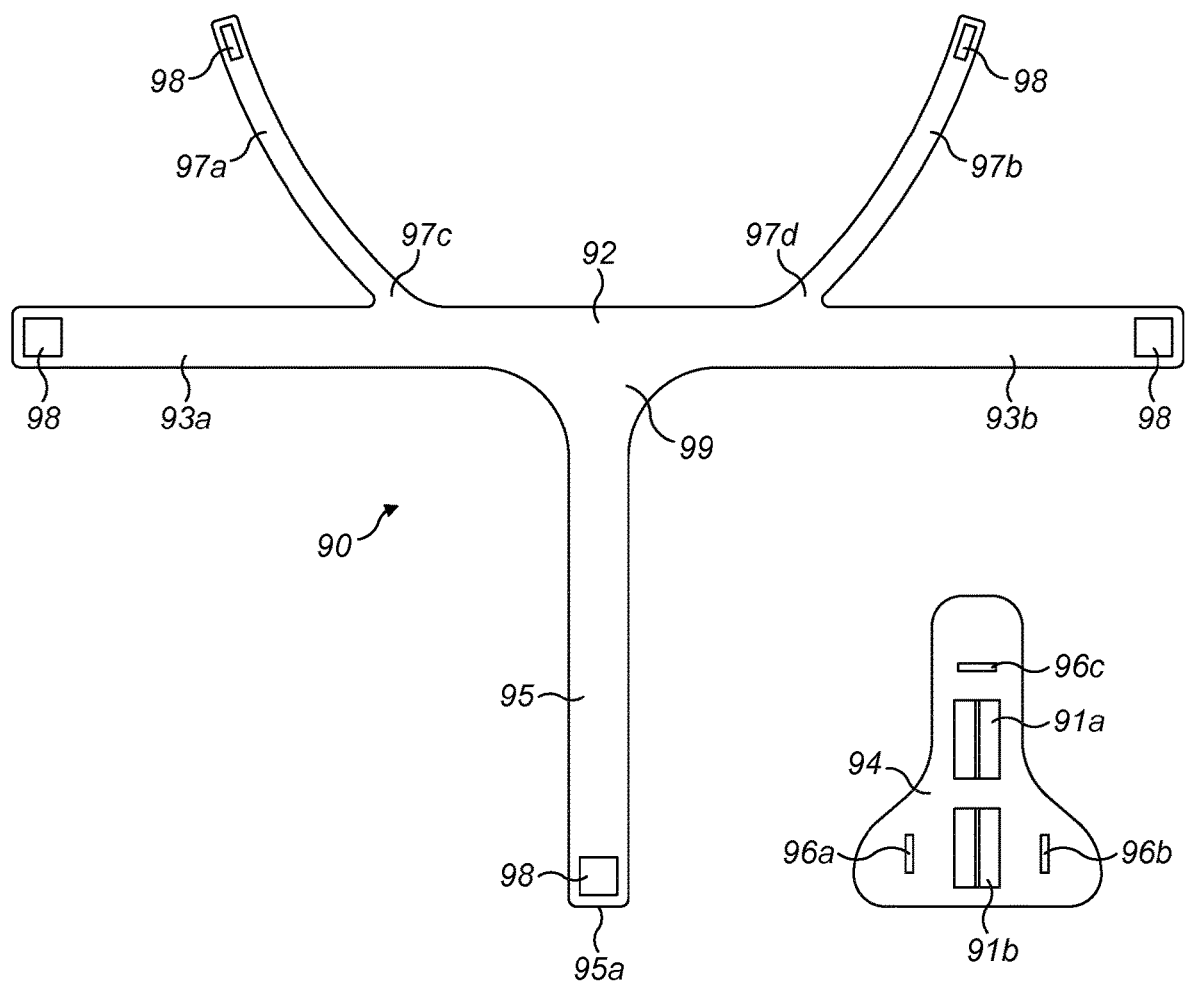
FIG. 8 shows a fixation device according to an embodiment of the invention.

The fixation device 90 includes a first part 92 and a separately provided second part 94 as shown in FIG. 8. The first part 92 includes a central portion 99 having five arms 93*a*, 93*b*, 95, 97*a*, 97*b* extending therefrom. A first side arm 93*a* and a second side arm 93*b* are diametrically opposed from one another either side of the central portion 99. A single rear arm 95 extends from the central portion 99 at approximately 90° from the first and second side arms 93*a*, 93*b*. First and second attachment arms 97*a*, 97*b* extend from the first and second side arms 93*a*, 93*b* from points 97*c*, 97*d* on either side of the central portion 99. The first and second side arms 93*a* and 93*b* may be the same length. Optionally, the rear arm 95 may also be the same length as the first and second side arms 93*a*, 93*b* or within 10% of the length thereof.

The side arms 93a, 93b, rear arm 95, and attachment arms 97*a*, 97*b* of the first part each have attachment portions 98 at their respective ends (ends distal from central portion 99). The attachment portion 98 of each arm allows the end of that arm to be attached to multiple positions on an intermediate portion of that arm in order to form loops of adjustable size. In the illustrated embodiment, the arms of the first part 92 are made from double-sided brush nylon and the attachment portions 98 are made from a hook material for engagement with the nylon.

The second part 94 is generally T-shaped (or triangular) and includes three slots 96*a*, 96*b*, 96*c* at each end of the T for engagement with the loops formed by the arms of the first part 92. More particularly, the side arms 93*a*, 93*b* engage with the diametrically opposed first and second slots 96*a*, 96*b* and the rear arm 95 engages with the third slot 96*c*. The slots 96*a* and 96*b* may be parallel to one another and the slot 96*c* may be aligned substantially perpendicular to slots 96*a* and 96*b*.

The second part also includes two tube fixation means 91*a*, 91*b* for attachment to the conduit system 40 of the ventilation system 10. In the embodiment illustrated in FIG. 9A, the fixation means 91*a*, 91*b* include hook and loop material, however, it will be appreciated that other fixation means such as adhesive means, clip or clamps could also be used. It will be further appreciated that any number of tube fixation means could be used.

Figure 9A:
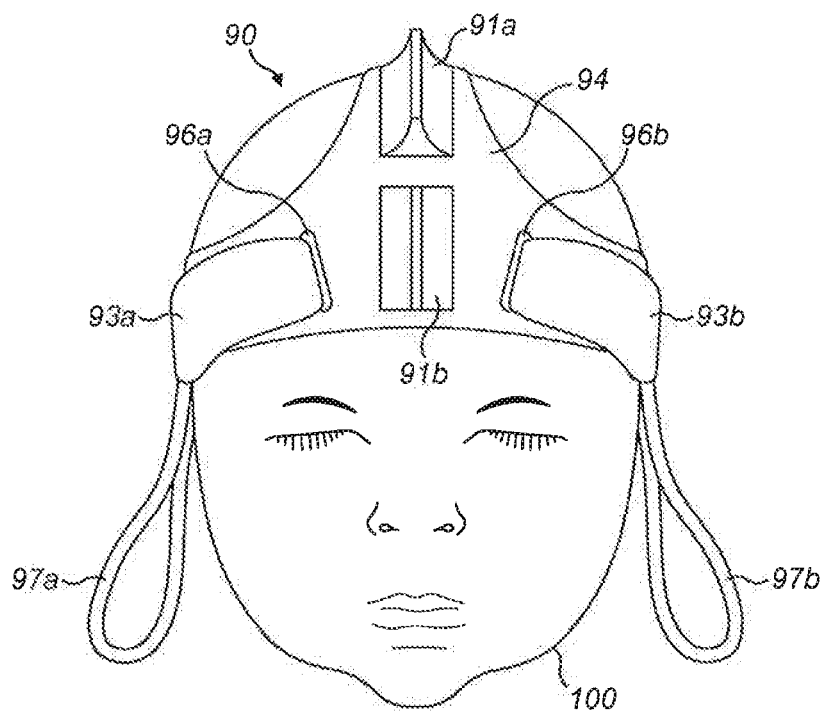
FIG. 9A shows a front view of the fixation device of FIG. 8 mounted to the head of an infant.
Figure 9B:
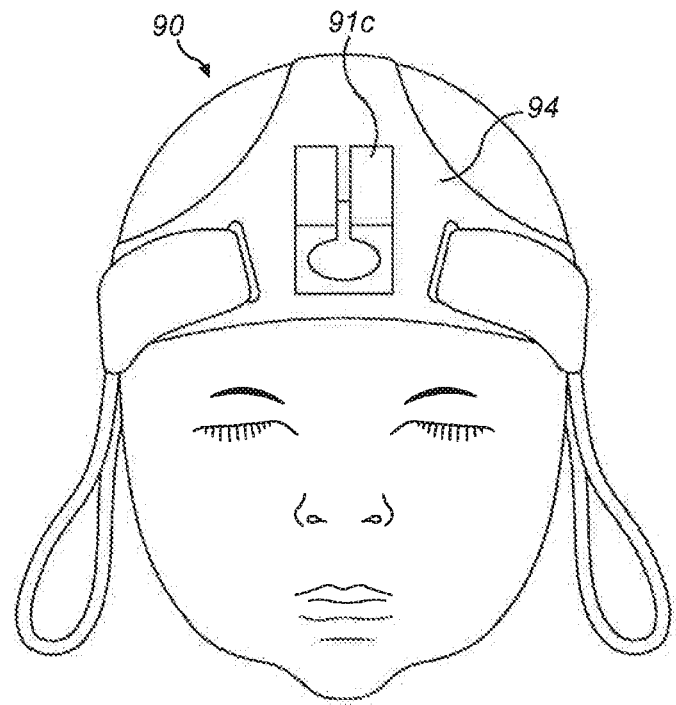
FIG. 9B shows a front view of an alternative embodiment of the fixation device of FIG. 9A.
Figure 9C:
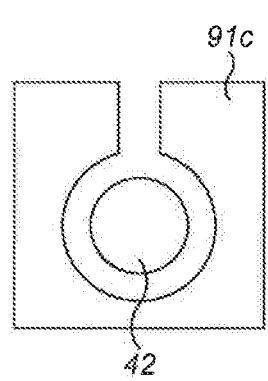
FIGS. 9C and 9D show a cross-sectional view of fixation means of the fixation device of FIG. 9B.
Figure 9D:
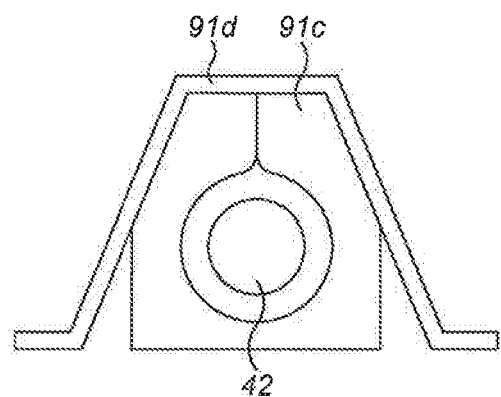
Figure 9E:
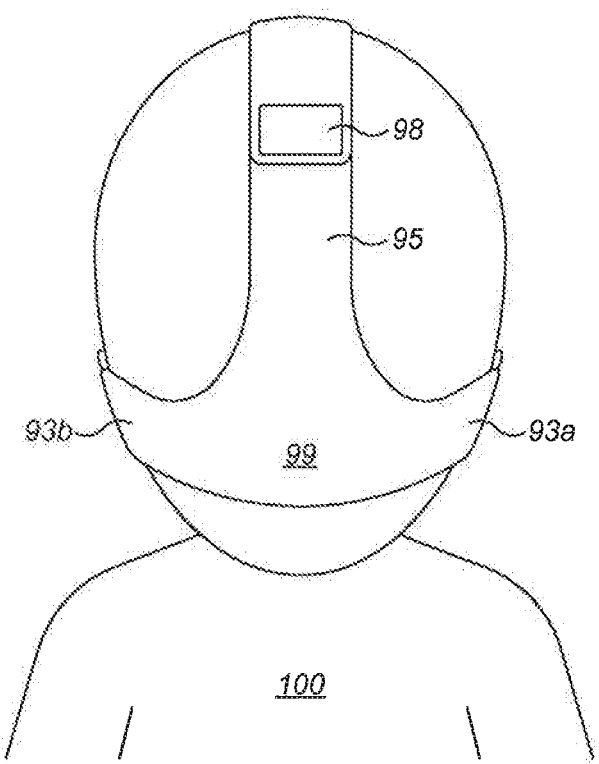
FIG. 9E shows a rear view of the fixation device of FIG. 8 mounted to the head of an infant.

FIG. 9B shows an alternative embodiment of the fixation device 90 of FIG. 9A, in which the fixation means comprises a removable fixation member 91*c*. The removable fixation member 91*c* is shown in cross-section in FIG. 9C. The removable fixation member is a substantially U-shaped block, forming an opening for receiving a tube of the conduit system 40. The member 91*c* removably attaches to the second part 94. The member 91*c* may be made of a foam material comprising a hook/loop fastening tape base for affixing to a complementary surface on the second part 94. Alternatively, other materials may be used to form the member 91*c* and/or the member may be differently attached to the second part 94. As shown in FIG. 9D, the fixation device 90 may further comprise tape 91*d* attached to the second part 94, overlying the removable fixation member 91*c* and covering the opening. The tape 91*d* may compress the fixation member 91*c* and secure the tube of the conduit system 40 therein. The fixation member 91*c* may securely hold the tube in place and prevent any twisting of the tube relative to the patient.

In use, the central portion 99 of the first part 92 is positioned behind the head of the infant adjacent the nape of the neck. The second part 94 is positioned on the forehead of the infant such that the diametrically opposed slots 96*a*, 96*b* are above and generally aligned with the eyebrows of the infant. The free end 95*a* of the rear arm 95 is inserted through the third slot 96*c* and doubled back on itself and secured to an intermediate portion of the back arm 95.

First and second side arms 93*a*, 93*b* are inserted through first and second slots 96*a*, 96*b* and secured to themselves in a similar manner.

First and second attachment arms 97*a*,97*b* therefore extend from the ear region of the infant as shown in FIG. 8 and can each form loops for attachment to the patient interface device.

The fixation device is sized to fit head circumferences of 17 cm-42 cm. A number of fixation devices of different sizes may be provided in a kit. For example, the fixation devices may come in a set of 5 or 6 devices of varying sizes to suit a broad range of head circumferences.

Figure 11C:
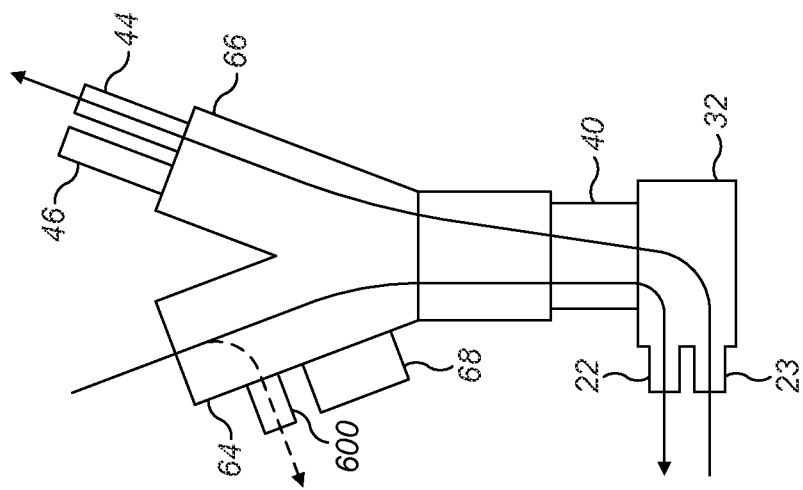
FIG. 11C shows a schematic diagram of flow though the ventilation system during resuscitation when the patient's lungs are inflated.
Figure 11B:
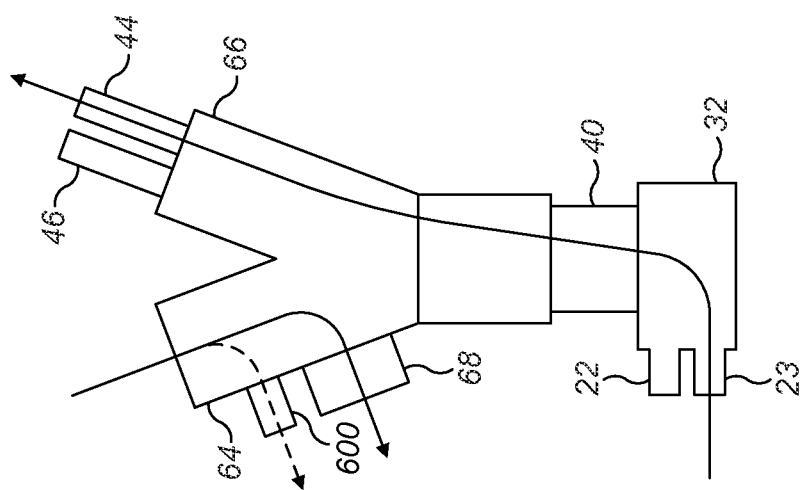
FIG. 11B shows a schematic diagram of flow through the ventilation system during resuscitation when the patient's lungs are deflated in an alternative configuration.
Figure 11A:
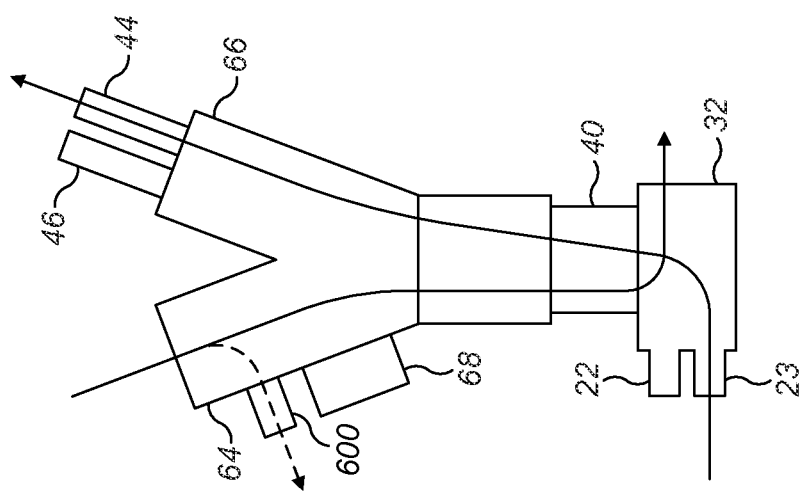
FIG. 11A shows a schematic diagram of flow though the ventilation system during resuscitation when the patient's lungs are deflated.
Figure 12:
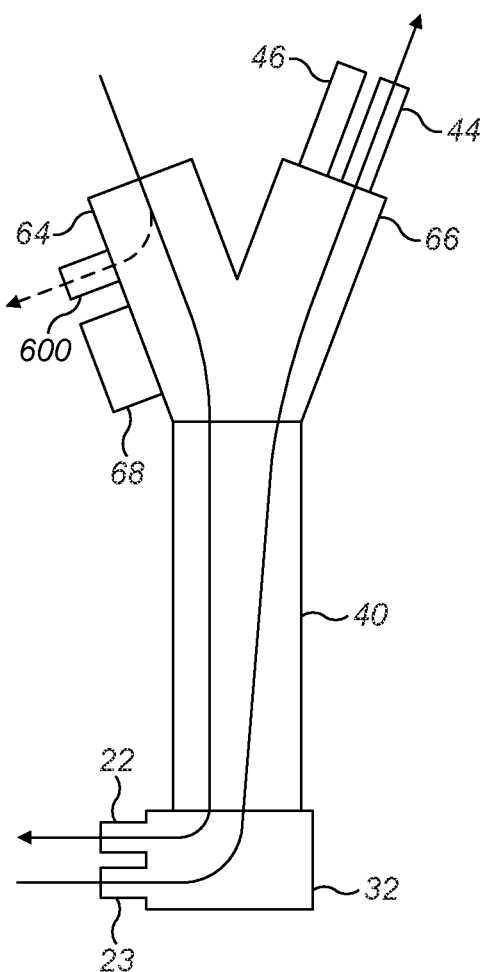
FIG. 12 shows a schematic diagram of flow though the ventilation system during highflow therapy.

FIGS. 10 to 12 are schematic diagrams showing the ventilation system in various modes of respiratory therapy. CPAP (e.g. nCPAP) Configuration The ventilator system 10 as described above may be configured to deliver CPAP or nCPAP therapy to a patient by the following method.

In a CPAP configuration, an air ssource 200 is fluidly coupled with the second body 70 of the connector system 60 via the second gas line 46 extending through the third port 66. A pressure monitoring device 300 is fluidly coupled with the connector system 60 via the third gas line 44 extending through the third port 66. An air exhaust line is connected to the connector system 60 via one of the second port 64 or auxiliary exhaust port 32. The fourth port 68 is closed with the removable second closure 69. The auxiliary exhaust port 32 of the patient interface device may also be closed by the removable first closure 33.

Figure 10C:
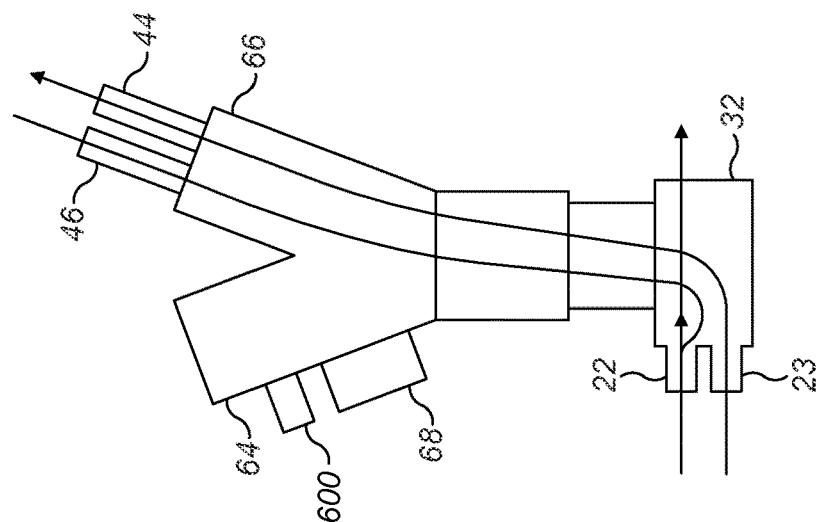
FIG. 10C shows a schematic diagram of flow though the ventilation system during CPAP therapy when the patient is exhaling, in an alternative configuration.
Figure 10B:
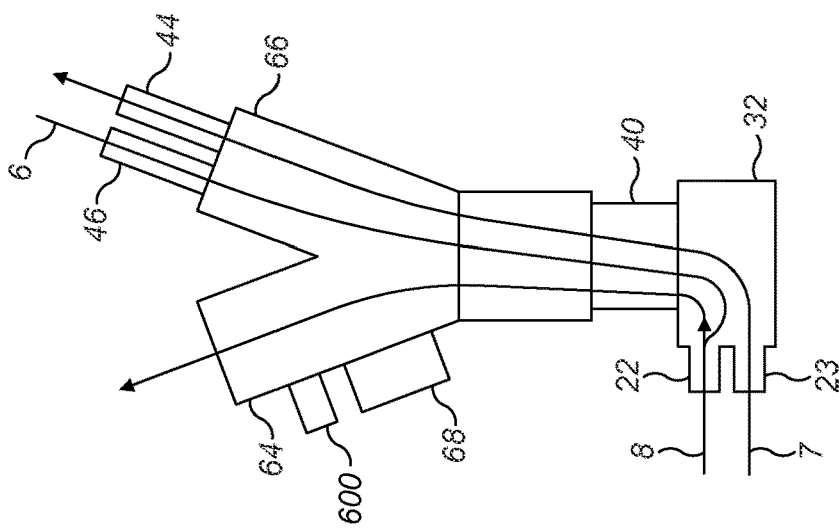
FIG. 10B shows a schematic diagram of flow though the ventilation system during CPAP therapy when the patient is exhaling.
Figure 10A:
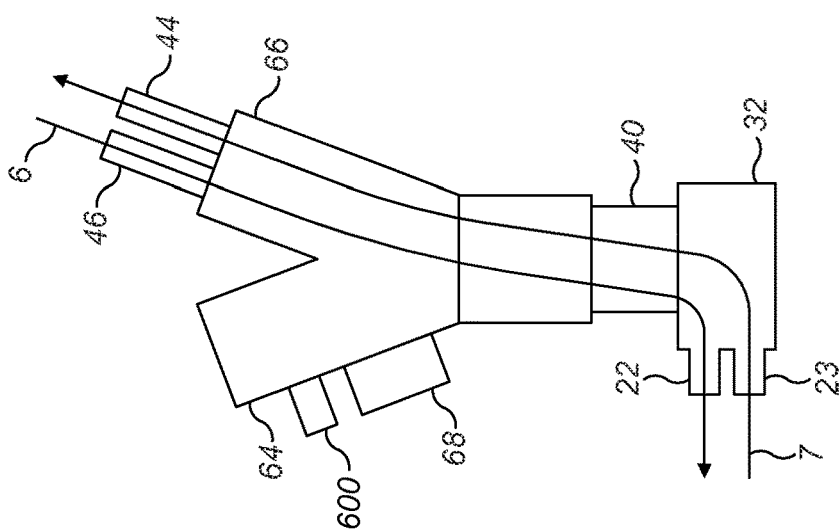
FIG. 10A shows a schematic diagram of flow though the ventilation system during CPAP therapy when the patient is inhaling.

FIGS. 10A-C show the flow through the ventilator system configured to deliver CPAP. FIG. 10A shows respiratory gas flow 6, pressure monitor flow 7 through the system when the patient is breathing in (inhaling). Respiratory gas flow 6 enters the system 10 via the second gas line 46 in the third port and is directed though the conduit system 40 and to the patient via air outlets 22. In this mode either second port 64 or auxiliary exhaust 32 may be open.

FIGS. 10B and 10C show flow of exhaled air 8 through the system 10 when the patient is breathing out (exhaling) in alternative system configurations. In FIG. 10B second port 64 is open and connected to an exhaust and auxiliary exhaust 32 is closed. Exhaled air 8 from the patient enters the system via air outlets 22 and collides with the respiratory gas flow 6 path.

The greater pressure and/or flow rate of the exhaled air 8 diverts the respiratory gas flow path 6 from the hole 29 in to the cavity 36 such that both the exhaled air 8 and supply gas exit the system as exhaust gas 9 via the second port 64. In FIG. 10C, the auxiliary exhaust 32 is connected to a first gas line. Exhaled air 8 and supply gas 6 flow into the cavity 36 and then exit the system via the auxiliary exhaust 32.

The fourth port 68 is closed in the CPAP configuration described above. However, in a further CPAP configuration, the fourth port 68 may be used as an exhaust instead of the second port 64 or auxiliary exhaust.

In arrangements where the second port 64 is not used for exhaust gas (such as when the auxiliary exhaust 32 or fourth port 68 is used for exhaust), the second port 64 may be connected to a further air supply (not shown). The further air supply may be isolated from the system by a switch, valve or flow prevention means during the first mode. Once the further gas supply is switched on the initial gas supply may be switched off or may remain in fluid communication with the system. This embodiment allow switching between modes simply by actuating a switch or valve of the further gas supply and requires no reconnection of the conduit system or gas supplies between modes.

The pressure relief valve 400 may be used. The pressure relief valve 400 may be mounted on the connector system or anywhere else on the assembly where it can function to control the maximum pressure in the system.

Resuscitation Configuration

In a resuscitation configuration, a high flow air supply is fluidly connected to the connector system 60 via the second port 64. A pressure monitoring device 300 is connected to the connector system 60 via the third gas line 44 extending through the third port 66. The second gas line 46 is closed by a valve such as the closure described in relation to the second body 70 above.

In a first arrangement (as shown in FIG. 5), the fourth port 68 is opened by removing the removable second closure 69 and the auxiliary exhaust port 32 of the patient interface device is closed by the removable first closure 33.

In a second arrangement, the fourth port 68 is closed with the removable second closure 69 and the auxiliary exhaust port 32 of the patient interface device is opened by removing the removable first closure 33.

In resuscitation mode, the nasal prong device may be replaced with a resuscitation mask.

FIGS. 11A-C show the flow through the ventilator system 10 configured to deliver resuscitation breaths to the patient. FIGS. 11A and 11B show alternative configurations for when the patient's lungs are deflating. In the configuration of FIG. 11A the fourth port 68 is closed and the auxiliary exhaust is open. As the lungs deflate, supply gas thus escapes from the system via the auxiliary exhaust 32. In the configuration of FIG. 11B the fourth port 68 is open and the auxiliary exhaust 32 is closed. Supply air thus escapes from the system via the fourth port.

FIG. 11C shows the flow through the system when the lungs are being inflated. Both the fourth port 68 and the auxiliary exhaust 32 are now closed such that air is directed to the patient at maximum pressure and flow rate. The port 68 and/or auxiliary exhaust 32 may be closed manually or via a valve to control the transition between inflation breaths and allowing deflation.

Highflow Configuration

In a highflow therapy configuration, a high flow air supply is fluidly coupled with the first body 61 of the connector system 60 via the second port. A pressure monitoring device 300 is fluidly coupled with the second body 70 of the connector system 60 via first outlet 72. Second outlet 74 is closed with a removable third closure 75.

The fourth port 68 is closed with the removable second closure 69 and the auxiliary exhaust port 32 of the patient interface device is closed with the removable firt closure 33. The nasal prongs of the patient interface device are held loosely inside or adjacent the nares of the patient (i.e. not in sealing contact therewith).

FIG. 12 show flow through the ventilation system 10 configured to deliver highflow therapy to the patient.

| Mode | Valve | | | | |
|---|---|---|---|---|---|
| | Third gas line 44 | Second gas line 46 | Second Port 64 | Fourth Port 68 | Auxiliary Exhaust 32 |
| nCPAP Patient Breathing In | Pressure Monitor | Open- connected to gas supply | Open/ closed | closed | Open/ closed |
| nCPAP Patient Breathing Out (1) | Pressure Monitor | Open - connected to gas supply | Open - connected to exhaust | closed | closed |
| nCPAP Patient Breathing Out (2) | Pressure Monitor | Open - connected to gas supply | closed | closed | Open - connected to exhaust |
| nCPAP Patient Breathing Out (3) | Pressure Monitor | Open - connected to gas supply | closed | Open - connected to exhaust | closed |
| Resuscitation Lung Deflation (1) | Pressure Monitor | closed | Open - connected to gas supply | closed | Open - connected to exhaust |
| Resuscitation Lung Deflation (2) | Pressure Monitor | closed | Open - connected to gas supply | Open - connected to exhaust | closed |
| Resuscitation Lung Inflation | Pressure Monitor | closed | Open - connected gas supply | closed | closed |
| Highflow | Pressure Monitor | closed | Open - connected | closed | closed |

-continued

| Mode | Valve | | | | |
|---|---|---|---|---|---|
| | Third gas line 44 | Second gas line 46 | Second Port 64 | Fourth Port 68 | Auxiliary Exhaust 32 |
| | | | | | to gas supply |

The ventilation system 10 is therefore capable of providing respiratory therapy in at least three modes i.e. nCPAP, highflow and resuscitation. A practitioner can deliver various modes of respiratory therapy using a single system.

For example, an infant may be receiving nCPAP therapy for respiratory stress syndrome. If the infant then becomes critical, the practitioner can easily provide resuscitation by adjusting the inputs and outputs as described above. Alternatively, an infant may require resuscitation immediately after birth and then subsequently require breathing support either via CPAP or high flow therapy. Additionally or alternatively, an infant may start respiratory therapy with CPAP and the practitioner may wish to switch to high flow therapy as the infant's condition changes or improves and vice versa.

The invention claimed is:

1. A ventilation system for delivering respiratory therapy to a patient, the ventilation system comprising:
   a patient interface device for delivering pressurized respiratory gas to a patient;
   a connector system for connection to a source of pressurized respiratory gas, the connector system comprising a hollow body having a cavity therein;
   a conduit system fluidly connecting the connector system to the patient interface device, wherein the conduit system includes a first gas line and a second gas line, and the second gas line is positioned within the first gas line for a length of the second gas line which extends between the patient interface device and the connector system;
   a first valve forming a pressure relief valve configured to control a maximum pressure of the respiratory gas in the system; and
   a plurality of closable ports that allow a plurality of different modes of respiratory therapy to be provided, the plurality of closable ports comprising:
      a first closable port in the hollow body for connection to the source of pressurized respiratory gas; and
      a second closable port forming an exhaust port closable manually or via a second valve;
   wherein, in a first mode, the second gas line provides respiratory gas to the patient interface device and the first gas line provides an exhaust channel to remove exhaled gases from the ventilation system by venting exhaled gas through the exhaust port and, in a second mode, respiratory gas is supplied via the first closable port such that the first gas line provides respiratory gas to the patient interface device and the exhaust port is closed manually or via the second valve such that respiratory gas is directed to the patient at the maximum pressure.

2. The system of claim 1, wherein the conduit system includes a third gas line, the third gas line is positioned within the first gas line along at least part of its length, and the third gas line is configured for connection to a pressure monitor such that a pressure at the patient interface device can be monitored.

3. The ventilation system of claim 2, wherein the third gas line extends from the patient interface device to the body of the connector system, the third gas line terminating at the connector system and connecting to a conduit within the connector system.

4. The ventilation system of claim 2, wherein the third gas line extends from the patient interface device and through the body of the connector system for connection to the pressure monitor.

5. The ventilation system of claim 4, wherein the connector system further comprises a distal port at a distal end of the hollow body, the first gas line, second gas line and third gas line extending from the distal port to the patient interface device, the first closable port positioned at an opposed end of the hollow body to the distal port.

6. The ventilation system of claim 5, wherein the first gas line terminates at the distal port and the second gas line extends through the distal port and the connector system.

7. The ventilation system of claim 6, wherein the second gas line extends through a sealed port of the connector system for connection to a source of air, the sealed port positioned at the opposed end of the hollow body to the distal port.

8. The ventilation system of claim 1, wherein, in the second mode, the second gas line is closed by one of the plurality of closable ports.

9. The ventilation system of claim 1, further comprising a fixation device for securing the patient interface device to the head of a patient.

10. The ventilation system of claim 1, wherein the pressure relief valve is mounted on the connector system.

11. The ventilation system of claim 1, wherein the pressure relief valve forms part of a source of pressurized respiratory gas connected to the first port.

* * * * *